US011457806B2

(12) United States Patent
Puyo et al.

(10) Patent No.: US 11,457,806 B2
(45) Date of Patent: Oct. 4, 2022

(54) METHODS AND DEVICES FOR FULL-FIELD OCULAR BLOOD FLOW IMAGING

(71) Applicants: CENTRE NATIONAL DE LA RECHERCHE SCIENTIFIQUE (CNRS), Paris (FR); ECOLE SUPÉRIEURE DE PHYSIQUE ET DE CHIMIE INDUSTRIELLES DE LA VILLE DE PARIS, Paris (FR); INSTITUT NATIONAL DE LA SANTE ET DE LA RECHERCHE MEDICALE (INSERM), Paris (FR); SORBONNE UNIVERSITE, Paris (FR)

(72) Inventors: Léo Puyo, Longevilles-sur-Mer (FR); Michael Atlan, Paris (FR)

(73) Assignees: CENTRE NATIONAL DE LA RECHERCHE SCIENTIFIQUE (CNRS), Paris (FR); ECOLE SUPÉRIEURE DE PHYSIQUE ET DE CHIMIE INDUSTRIELLES DE LA VILLE DE PARIS, Paris (FR)

( * ) Notice: Subject to any disclaimer, the term of this patent is extended or adjusted under 35 U.S.C. 154(b) by 453 days.

(21) Appl. No.: 16/730,555

(22) Filed: Dec. 30, 2019

(65) Prior Publication Data

US 2021/0196120 A1 Jul. 1, 2021

(51) Int. Cl.
*G06K 9/00* (2022.01)
*A61B 3/12* (2006.01)
(Continued)

(52) U.S. Cl.
CPC .......... *A61B 3/1241* (2013.01); *A61B 3/0025* (2013.01); *G06T 7/0016* (2013.01);
(Continued)

(58) Field of Classification Search
CPC ... A61B 3/1241; A61B 3/0025; A61B 5/7203; A61B 5/7257; A61B 5/0075;
(Continued)

(56) References Cited

U.S. PATENT DOCUMENTS 10,571,243 B2 * 2/2020 Everett ................ A61B 3/1225
11,262,191 B1 * 3/2022 Millerd .............. G01B 9/02057
(Continued)

FOREIGN PATENT DOCUMENTS

FR 2 947 064 B1 1/2012
FR 2963117 A1 * 1/2012 ........... G03H 1/0443

OTHER PUBLICATIONS

T. Desmettre et al; "Fluorescence Properties and Metabolic Features of Indocyanine Green (ICG) as Related to Angiography"; Survey of Ophthalmology, vol. 45, No. 1, pp. 15-27; Jul. 15, 2000 (13 pages).
(Continued)

*Primary Examiner* — Shervin K Nakhjavan
(74) *Attorney, Agent, or Firm* — Osha Bergman Watanabe & Burton LLP

(57) ABSTRACT

According to a first aspect, the present disclosure relates to a digital holography device (100) for full-field blood flow imaging of ocular vessels of a field of view of a layer (11) of the eye (10). The device comprises an optical source (101) configured for the generation of an illuminating beam (Eobj) and a reference beam ($E_{LO}$), and a detector (135) configured to acquire a plurality of interferograms (I(x,y,t)) wherein an interferogram is defined as the signal resulting from the interference between the said reference beam ($E_{LO}$) and a part of said illuminating beam (Eobj) that is backscattered from said layer (11). The device further comprises a processing unit (150) configured for processing said plurality of interferograms, (I(x,y,t)), wherein said processing comprises: the calculation (202), for each interferogram, of a
(Continued)

hologram (H(x,y,t)), resulting in a first plurality of holograms; the selection (203), in sequential time windows, (tw), of second pluralities of holograms; the calculation (204), for each said second plurality of holograms, of a Doppler power spectrum (S(x,y,f)); the calculation (205), based on said Doppler power spectrum, of at least a first Doppler image thus generating at least a first plurality of Doppler images; the processing of each first Doppler image, wherein said processing comprises the devignetting (206) of said first Doppler image, resulting in a devignetted first Doppler image; the normalization (207) of said devignetted first Doppler image based on a spatial average of an intensity of said first Doppler image, resulting in a normalized first Doppler image; and the subtraction (208), from said normalized first Doppler image, of said spatial average of said intensity of said first Doppler image, resulting in a corrected first Doppler image.

16 Claims, 11 Drawing Sheets

(51) Int. Cl.
  *A61B 3/00* (2006.01)
  *G06T 11/00* (2006.01)
  *G06T 7/00* (2017.01)
  *A61B 5/00* (2006.01)
(52) U.S. Cl.
  CPC ........... *G06T 11/005* (2013.01); *A61B 5/7203* (2013.01); *A61B 5/7257* (2013.01); *G06T 2207/10064* (2013.01); *G06T 2207/20224* (2013.01); *G06T 2207/30041* (2013.01); *G06T 2207/30104* (2013.01); *G06T 2211/404* (2013.01)
(58) Field of Classification Search
  CPC . A61B 5/02007; G06T 7/0016; G06T 11/005; G06T 2207/10064; G06T 2207/20224; G06T 2207/30041; G06T 2207/30104; G06T 2211/404
  See application file for complete search history.

(56) References Cited

U.S. PATENT DOCUMENTS

| | | | |
|---|---|---|---|
| 2010/0245836 A1* | 9/2010 | Kulkarni | G01B 9/02091 356/479 |
| 2014/0180075 A1* | 6/2014 | Kulkarni | A61B 3/102 356/450 |
| 2016/0206193 A1* | 7/2016 | Schmoll | A61B 3/0025 |

OTHER PUBLICATIONS

A. D. Pechauer et al; "Assessing total retinal blood flow in diabetic retinopathy using multiplane en face Doppler optical coherence tomography"; British Journal of Ophthalmology, vol. 102, No. 1, pp. 126-130; May 11, 2017 (13 pages).

T. Sugiyama et al; "Use of laser speckle flowgraphy in ocular blood flow research"; Acta Ophthalmologica, vol. 88, No. 7, pp. 723-729; Sep. 9, 2009 (7 pages).

L. Puyo et al;. "In vivo laser Doppler holography of the human retina"; Biomedical Optics Express, vol. 9, No. 9, pp. 4113-4129; Aug. 6, 2018 (17 pages).

J. W. Goodman; "Introduction to Fourier Optics" 2nd Ed. McGraw Hill, pp. 55-61; Columbus, OH, 1996 (7 pages).

F. Leong, et al; "Correction of uneven illumination (vignetting) in digital microscopy images"; Journal of Clinical Pathology, vol. 56, No. 8, pp. 619-621; Jul. 30, 2003 (3 pages).

J. Baranger et al; "Adaptive Spatiotemporal SVD Clutter Filtering for Ultrafast Doppler Imaging Using Similarity of Spatial Singular Vectors"; IEEE Transactions on Medical Imaging, vol. 37, No. 7, pp. 1574-1586; Feb. 5, 2018 (13 page).

D. Hillmann, et al; "Aberration-free volumetric high-speed imaging of in vivo retina"; Scientific Reports 6, 35209; Oct. 20, 2016 (11 pages).

L. Ginner et al; "Noniterative digital aberration correction for cellular resolution retinal optical coherence tomography in vivo"; Optica, vol. 4, No. 8, pp. 924-931; Aug. 1, 2017 (8 pages).

M. Atlan et al; "Frequency-domain wide-field laser Doppler in vivo imaging"; Optics Letters, vol. 31, No. 18, pp. 2762-2764; Aug. 25, 2006 (3 pages).

M. Atlan et al; "High-speed wave-mixing laser Doppler imaging in vivo"; Optics Letters, vol. 33, No. 8, pp. 842-844; Apr. 14, 2008 (3 pages).

M. Simonutti et al; "Holographic laser Doppler ophthalmoscopy"; Optics Letters, vol. 35, No. 12, pp. 1941-1943; Jun. 3, 2010 (3 pages).

M. Pellizzari et al; "High speed optical holography of retinal blood flow"; Optics Letters, vol. 41, No. 15, pp. 3503-3506; Jul. 25, 2016 (4 pages).

L. Puyo et al; "Choroidal vasculature imaging with laser Doppler holography"; Biomedical Optics Express, vol. 10, No. 2, pp. 995-1012; Jan. 31, 2019 (18 pages).

L. Puyo et al; "Waveform analysis of human retinal and choroidal blood flow with laser Doppler holography" Biomedical Optics Express, vol. 10, No. 10, p. 4942-4963; Sep. 5, 2019 (22 pages).

* cited by examiner

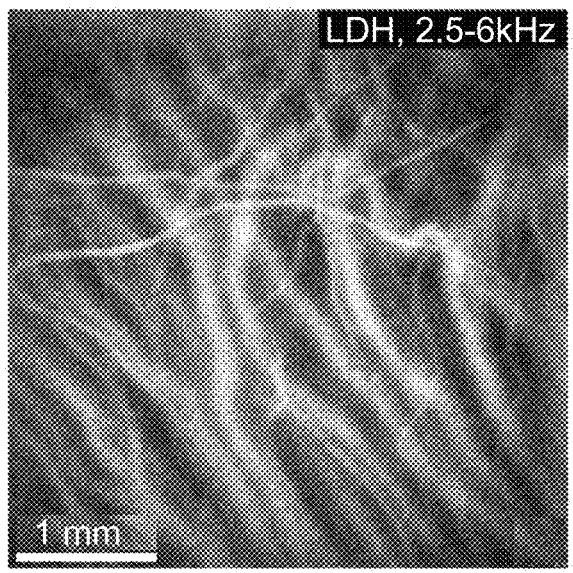
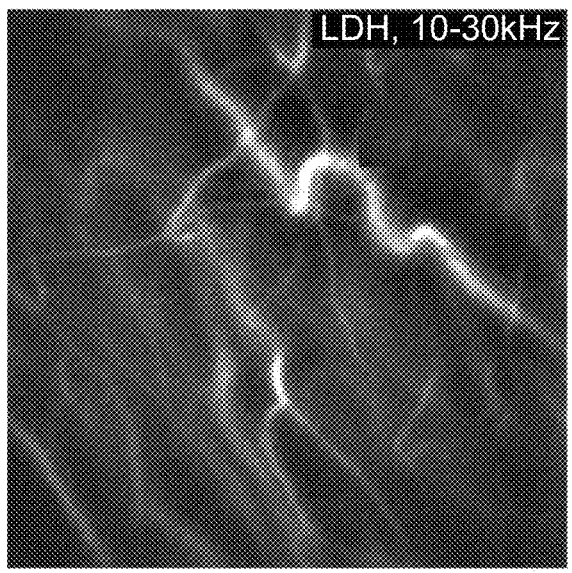
FIG.4A  FIG.4B
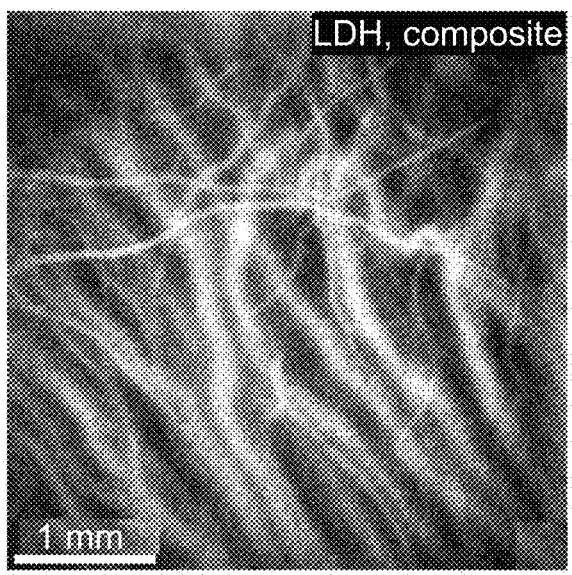
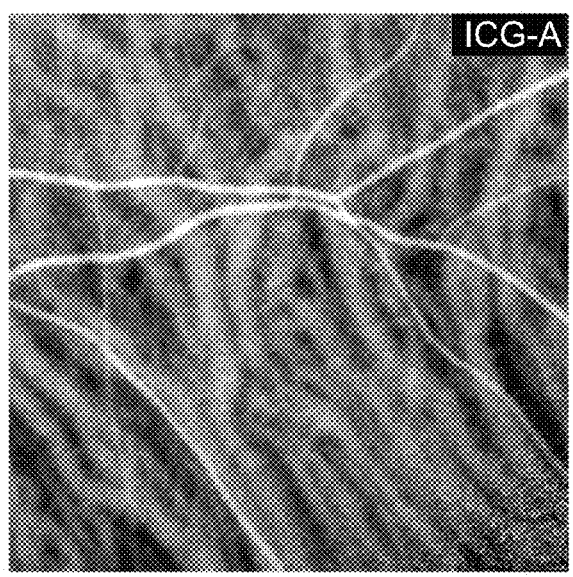
FIG.4C  FIG.4D

METHODS AND DEVICES FOR FULL-FIELD OCULAR BLOOD FLOW IMAGING

TECHNICAL FIELD OF THE INVENTION

The invention relates to methods and devices for full-field imaging of blood flows in the eye using, in particular, laser Doppler holography.

PRIOR ART

Precise monitoring of ocular blood flows is used to understand and diagnose major eye-related diseases such as central and branch retinal vein and artery occlusions, central serous chorioretinopathy, diabetic retinopathy, hypertensive retinopathy, age-related macular degeneration, and glaucoma. Typically, these diseases affect the microscopic structure of the ocular vessels in various retinal and choroidal layers, and blood flow dynamics. Detecting them requires imaging techniques with a sufficient spatial resolution (better than 10 microns) and a time resolution below the typical timescale of the blood flow dynamics (below the second).

Fluorescein angiography (FA) and indocyanine-green angiography (ICGA) are popular methods to study the ocular blood flows, as disclosed in Desmettre et al. "*Fluorescence properties and metabolic features of indocyanine green (ICG) as related to angiography*" Survey of ophthalmology 45.1 (2000):15-27. They are based on the use of a fluorescent contrast agent that circulates in the ocular vessels and reveals the vasculature of the choroid and retina. However, non-invasive techniques are preferred to limit risk or inconvenience for the patients.

Nowadays, most state-of-the-art non-invasive instruments used for ocular blood flow measurement rely on the measurement of random intensity fluctuations (speckle) originating from the interference between multiple light fields backscattered by moving objects (scatterers) present in illuminated ocular layers, typically red blood cells. As the spatial contrast depends on the velocity of the scatterers, it is possible to retrieve information on the ocular blood flow.

Optical Coherence Tomography Angiography (OCT-A), as described in Pechauer et al. "*Assessing total retinal blood flow in diabetic retinopathy using multiplane en face Doppler optical coherence tomography*" British Journal of Ophthalmology 102.1 (2017): 126-130, is a powerful blood flow imaging technique that uses the speckle variations in the OCT signal caused by scatterers to generate a contrast image of ocular vessels by calculating the local variance of speckle over a few measurements. OCT-A instruments can map the retinal micro-vascular network with a micrometer axial resolution and can be used to measure parameters relevant to the development of diabetic retinopathy such as the size and distribution of capillaries and the extent of the foveal avascular zone, i.e. the retinal zone in the fovea that is devoid of retinal blood vessels. However, this technique can only image a particular ocular layer at a particular depth, and in order to acquire a full image of the retina, it is necessary to reconstruct the full volume of the retina by sweeping the depth of the sample. This process takes a time of the order of the second, and the temporal resolution of the technique is then not sufficient to obtain a time-resolved measurement of the ocular blood flow, that is typically evolving in timescales below the second.

Another known technique is laser speckle flowmetry (or flowgraphy) as described for example in Sugiyama et al. "*Use of laser speckle flowgraphy in ocular blood flow research*" Acta ophthalmologica 88.7 (2010): 723-729. Similarly to OCT-A, it provides information on the ocular blood flow by calculating, in an ocular image, the speckle pattern decorrelation rate induced by moving scatterers in the blood stream. This technique is successful in measuring the ocular blood flow in real-time (e.g. with a temporal resolution of 33 millisecond), but it does not have depth sectioning ability so that the contribution from different ocular layers is not clearly distinguishable, and the dynamic range of measured velocities is low.

Another known technique is laser Doppler flowmetry (LDF), where ocular blood flow is measured from the self-interference of the light backscattered by the ocular layers on a photodiode. In other words, by illuminating a sample with single-frequency light and analysing the spectral content of the backscattered light, an estimate of the ocular blood flow can be achieved. The main limitation of this method is that is can only monitor a single point of the sample. Scanning configurations that can potentially provide a wider field of view have not been successful, because the temporal resolution is not sufficient to sample the variations of blood flow occurring over cardiac cycles.

In order to obtain full-field measurements of ocular blood flows and with a better time resolution, a novel technique has emerged, called laser Doppler holography. This technique is disclosed in Puyo, L., et al. ("*In vivo laser Doppler holography of the human retina*" Biomedical optics express 9.9 (2018): 4113-4129) and relies on measuring the spectral content of the signal originating from the interference between a monochromatic reference beam and a Doppler-broadened beam backscattered by a layer (typically the retina or the choroid) of the eye. This technique bears some resemblance to laser Doppler flowmetry (LDF), but differs from the latter in that it is a full-field imaging technique, therefore no scanning of the field of view is required. This renders the technique fast and with a very short time resolution, which allows for time-resolved dynamic ocular blood flow imaging.

However, the technique described in the above article still suffers from a lack of quantitative retrieval of information regarding ocular blood flow.

The present disclosure describes a processing method of the interferograms obtained via laser Doppler holography that enables time-resolved and full-field measurement of blood flows in ocular layers, for example, in the retina and in the choroid, and that provides images where the contrast is quantitative, i.e. where the image intensity is linearly related to the ocular blood flow.

SUMMARY

In what follows, the term "comprise" is synonym of (means the same as) "include" and "contains", is inclusive and open, and does not exclude other non-recited elements. Moreover, in the present disclosure, when referring to a numerical value, the terms "about" and "substantially" are synonyms of (mean the same as) a range comprised between 80% and 120%, preferably between 90% and 110%, of the numerical value.

According to a first aspect, the present disclosure relates to a method for full-field blood flow imaging in ocular vessels in a field of view of at least a first layer of the eye, the method comprising:

the acquisition over time of a plurality of interferograms of said at least first layer using a laser Doppler holography technique, wherein said at least first layer is illuminated by a light beam;

the calculation, for each interferogram of said plurality of interferograms, of a hologram, wherein the hologram is defined by a complex amplitude of a light beam backscattered by said at least first layer in a given spatial plane, resulting in a first plurality of holograms;

the selection, in sequential time windows, of second pluralities of holograms from said first plurality of holograms;

the calculation, for each said second plurality of holograms, of a Doppler power spectrum;

the calculation, based on said Doppler power spectrum, of at least a first Doppler image, thus generating at least a first plurality of Doppler images associated with said plurality of sequential time windows;

the processing of each first Doppler image of said plurality of Doppler images, wherein said processing comprises:

the devignetting of said first Doppler image, resulting in a devignetted first Doppler image;

the normalization of said devignetted first Doppler image using a spatial average of an intensity of said first Doppler image, resulting in a normalized first Doppler image;

the subtraction, from said normalized first Doppler image, of said spatial average of said intensity of said first Doppler image, resulting in a corrected first Doppler image; and, the sequential assembling of said corrected first Doppler images to generate a movie showing an evolution over time of blood flows in said ocular vessels.

In the present disclosure, "blood flow" is understood as a metrics quantifying the velocity of scatterers present in blood vessels.

The applicant has demonstrated that, by virtue of the method thus described, Doppler images of ocular layers can be obtained from which information on ocular blood flows can be extracted. Notably, it is possible to obtain a corrected Doppler image where blood flow levels are expressed quantitatively in arbitrary units on a linear scale. For example, this allows for accessing to rheologic parameters of the blood vessels, such as viscosity, pressure field, or elasticity. The applicant also showed that, when assembling said Doppler images in a movie, dynamic time-resolved measurements of the ocular blood flows can be obtained, such as the temporal waveform profile of the ocular blood flow, also referred to as the pulsatile ocular blood flow. This parameter is an important clinical tool for investigating eye-related diseases.

According to one or further embodiments, the calculation of the Doppler images is made in a sliding manner, meaning that said second plurality of holograms is constantly changing over time. Each time when a new quantity of holograms is added to the calculation, the same quantity of hologram is removed from the calculation and the Doppler power spectrum is calculated on a different plurality of holograms.

According to one or further embodiments, the calculation of said at least first Doppler image is done by integration of the Doppler power spectrum over a first selected range of frequencies. By virtue of the integration of the Doppler power spectrum over said selected range of frequencies, the applicant showed that it is possible to retrieve information on the type of blood vessels that are present in the field of view of a layer of the eye, and to distinguish to which layer of the eye said vessels belong.

According to one or further embodiments, at least a first and a second Doppler images are calculated by integration of the Doppler power spectrum over at least two different selected range of frequencies. By virtue of the integration of the Doppler power spectrum over different selected ranges of frequencies, the applicant showed that it is possible to further distinguish the type of blood vessels present in the field of view of the layers of the eye under study.

Advantageously, said first and second Doppler images can be superimposed to form a composite image. The color scale of the two images can be different so that the type of blood vessels is clearly identifiable in the image. This can, for example, be used to represent and investigate the different behaviors of ocular blood flows during systolic and diastolic periods of the cardiac cycle.

According to one or further embodiments, the processing of the Doppler images further comprises calculating the opposite of each corrected first Doppler image and said movie is generated from the sequential assembling of said opposite of said corrected first Doppler images.

Advantageously, the applicant demonstrated that, for example in a specific case where said selected range of frequencies includes only frequencies below a given low frequency value, for example about 5 kHz, representing the opposite of the corrected first Doppler images instead of the corrected first Doppler images allows for accessing information on blood flows corresponding to frequencies beyond half of the frame rate of an optical sensor. This case is encountered when a slow camera is used to detect the interferogram, for example a camera whose frame rate is below about 10 kHz.

In the present disclosure a two-dimensional optoelectronic detector, also referred to as optical sensor in the present disclosure, with a frame rate below a given low frame rate value is referred to as a slow camera and an optical sensor with a frame rate above said low frame rate value is referred to as a fast camera. Said low frame rate value is for example about 10 kHz.

In the present description, the frame rate is defined by the number of images that the optical sensor can detect per second.

According to one or further embodiments, the method further comprises filtering the holograms of the second plurality of holograms to remove parasitic contributions and calculating said Doppler power spectrum based on the filtered holograms.

According to one or further embodiments, a singular value decomposition (SVD) of a 2D matrix can be performed, wherein said 2D matrix is generated from said second plurality of holograms, resulting in a plurality of singular values and singular vectors. The filtering of said second plurality of holograms is then made using said plurality of singular values and singular vectors, resulting in a second plurality of filtered holograms. The calculation of said Doppler power spectrum is made on said second plurality of filtered holograms.

The applicant has demonstrated that, by virtue for example of the SVD of the holograms, it is possible to separate the ocular blood flows, mainly originating from the motion of the red blood cells, and the parasitic contributions including, for example, bulk motion of the eye, technical noises, and spurious reflections from the anterior segment of the eye. The holograms can then be filtered by removing the identified parasitic contributions. Notably, this enhances significantly the spatial resolution of the Doppler images and the detectivity of low flows when compared to a case without the SVD.

According to one or further embodiments, the method further comprises a rephasing procedure to compensate refractive aberrations of the eye, wherein said rephasing procedure comprises:

the estimation of a corrective phase term from at least one Doppler image of the first plurality of Doppler images; and, the calculation, for each hologram of said first plurality of holograms, of a compensated hologram, wherein said calculation uses said corrective phase term.

The rephasing procedure may be performed such that:

in a first step, at least one Doppler image of the first plurality of Doppler images, calculated using the method according to the present disclosure, is used to estimate a corrective phase term; and, in a second step, the corrective phase term is used to calculate a compensated hologram from a hologram of said first plurality of holograms.

The applicant has demonstrated that, by virtue of the rephasing procedure it is possible to obtain corrected Doppler images with a significantly enhanced spatial resolution, irrespective of the quality of the optics of the eye under study. This allows for the measurement of ocular blood flows in smaller vessels.

According to one or further embodiments, said corrective phase term is expressed in terms of a linear combination of Zernike polynomials.

According to one or further embodiments, said estimation of a corrective phase term from said at least one Doppler image comprises an iterative procedure. Such an iterative procedure implies that the rephasing procedure is performed several times wherein the result of a rephasing procedure at a given time, i.e. a compensated hologram, is used in a further rephasing procedure at a later time.

According to one or further embodiments, said estimation of a corrective phase term from said at least one Doppler image comprises a digital wavefront estimation made on said Doppler image calculated using sub-apertures selected within a spatial Fourier transform of the holograms.

According to a second aspect, the present disclosure relates to a digital holography device for full-field imaging of ocular blood flow in vessels in a field of view of at least a first layer of the eye configured to implement one or further embodiments of the method according to the first aspect.

According to one or further embodiments, the device according to the second aspect comprises:

an optical source configured for the generation of an illuminating beam and a reference beam, wherein said illuminating beam is configured for illuminating said at least first layer;

a combining element configured for combining said reference beam and a part of said illuminating beam that is backscattered from said at least first layer;

a two-dimensional optoelectronic detector with a frame rate, configured to acquire a plurality of interferograms, wherein an interferogram is defined as the signal resulting from the interference between said reference beam and the part of said illuminating beam that is backscattered from the said at least first layer;

a processing unit configured for processing said plurality of interferograms, wherein said processing comprises:

the calculation, for each interferogram of said plurality of interferograms, of a hologram, wherein the hologram is defined by a complex amplitude of a light beam backscattered by said at least first layer in a given spatial plane, resulting in a first plurality of holograms;

the selection, in sequential time windows, of second pluralities of holograms from said first plurality of holograms;

the calculation, for each said second plurality of holograms, of a Doppler power spectrum;

the calculation, based on said Doppler power spectrum, of at least a first Doppler image thus generating at least a first plurality of Doppler images associated with said plurality of sequential time windows;

the processing of each first Doppler image of said plurality of Doppler images, wherein said processing comprises:

the devignetting of said first Doppler image, resulting in a devignetted first Doppler image;

the normalization of said devignetted first Doppler image based on a spatial average of an intensity of said first Doppler image, resulting in a normalized first Doppler image;

the subtraction, from said normalized first Doppler image, of said spatial average of said intensity of said first Doppler image, resulting in a corrected first Doppler image; and, the sequential assembling of said corrected first Doppler images to generate a movie showing an evolution over time of blood flows in said ocular vessels.

According to one or further embodiments, the device further comprises an optical element configured for changing the size of said field of view.

Advantageously, this optical element is retractable such that the field of view in the layer of the eye that is imaged can be changed easily without changing the other parameters of the device, and without requiring subsequent reoptimization of said parameters.

According to one or further embodiments, said two-dimensional optoelectronic detector is a camera of CCD or CMOS type.

According to one or further embodiments, the device comprises a two-dimensional optoelectronic detector whose frame rate is inferior to about 10 kHz.

According to a third aspect, the invention relates to a method for full-field blood flow imaging of ocular vessels in a field of view of at least a first layer of the eye, the method comprising the acquisition over time of at least two pluralities of interferograms of said at least first layer using a laser Doppler holography technique, wherein said at least two pluralities of interferograms are acquired at two different optical frequencies.

According to one or further embodiments, the method according to the third aspect further comprises:

for each plurality of interferograms of said at least two plurality of interferograms:

the calculation, for each interferogram of said plurality of interferograms, of a hologram, wherein the hologram is defined by a complex amplitude of a light beam backscattered by said at least first layer in a given spatial plane, resulting in a first plurality of holograms;

the selection, in sequential time windows, of second pluralities of holograms from said first plurality of holograms;

the calculation, for each said second plurality of holograms, of a Doppler power spectrum;

the calculation, based on said Doppler power spectrum, of at least a first Doppler image, thus generating at least a first plurality of Doppler images and a second plurality of Doppler images associated to each of said optical frequencies.

By virtue of said method, it is possible to calculate Doppler images generated from acquisition of interferograms at at least two different optical frequencies and retrieve depth-resolved images of blood flows in the retina and the choroid. More specifically, it is possible to discriminate local optical absorption from blood flow, because the dependence of absorption of pigmented areas with the optical wavelength differs from the dependence of the blood flow signal with the optical wavelength.

According to one or further embodiments, the method according to the third aspect further comprises the sequential assembling of said Doppler images to generate a movie showing an evolution over time of blood flows in said ocular vessels.

It is understood that any of the embodiments of the method described according to the first aspect can be applied to the method according to the third aspect, for example, the processing of the Doppler images.

According to a fourth aspect, the present disclosure relates to a laser holography device configured to implement the method according to the third aspect.

For example, a device according to the fourth aspect comprises:

an optical source configured for the generation of an illuminating beam and a reference beam, wherein said illuminating beam is configured for illuminating said at least first layer;

a combining element configured for combining the said reference beam and a part of said illuminating beam that is backscattered from said at least first layer;

a two-dimensional optoelectronic detector with a given frame rate, configured to acquire a plurality of interferograms, wherein an interferogram is defined as the signal resulting from the interference between the said reference beam and the part of said illuminating beam that is backscattered from the said at least first layer;

a processing unit configured for processing said plurality of interferograms.

According to one or further embodiments, a frequency of the optical source can be changed between at least two frequencies.

According to one or further embodiments, the change in the optical source frequency can, for example, be performed by switching or sweeping the frequency over time. For example, if the frequency of the optical source is switched between two frequencies, two interleaved pluralities of interferograms can be obtained, each corresponding to one of said frequencies. Each plurality of interferograms is then processed independently according to the present disclosure, resulting in two pluralities of Doppler images. Linear combination of the Doppler images of said pluralities of Doppler images can then be made, making it possible to obtain spectroscopic information on the ocular blood vessels present in said field of view. Especially in the case of the use of a slow camera, by virtue of this method, it is possible to discriminate local optical absorption from blood flow, because the dependence of absorption of pigmented areas with the optical wavelength differs from the dependence of the blood flow signal with the optical wavelength.

BRIEF DESCRIPTION OF DRAWINGS

Other advantages and features of the invention will become apparent on reading the description, illustrated by the following figures which represent:

FIGS. 4A and 4B, pictures showing Doppler images of the posterior layers of the eye (choroid and retina) obtained via an exemplary device according to the present disclosure, after integrating the Doppler power spectrum over different selected range of frequencies, centered at a lower (4A) or higher (4B) frequency; FIG. 4C, a composite image obtained after combining the said previous two Doppler images in a single image; FIG. 4D, Doppler image of the same layers of the eye obtained via the indocyanine-green angiography method, for comparison;

FIG. 8A shows a plot of the normalized singular values identified after SVD of a plurality of holograms; FIG. 8B shows two-dimensional representation of spatial eigenvectors with different indices;

DETAILED DESCRIPTION

Figure 1:
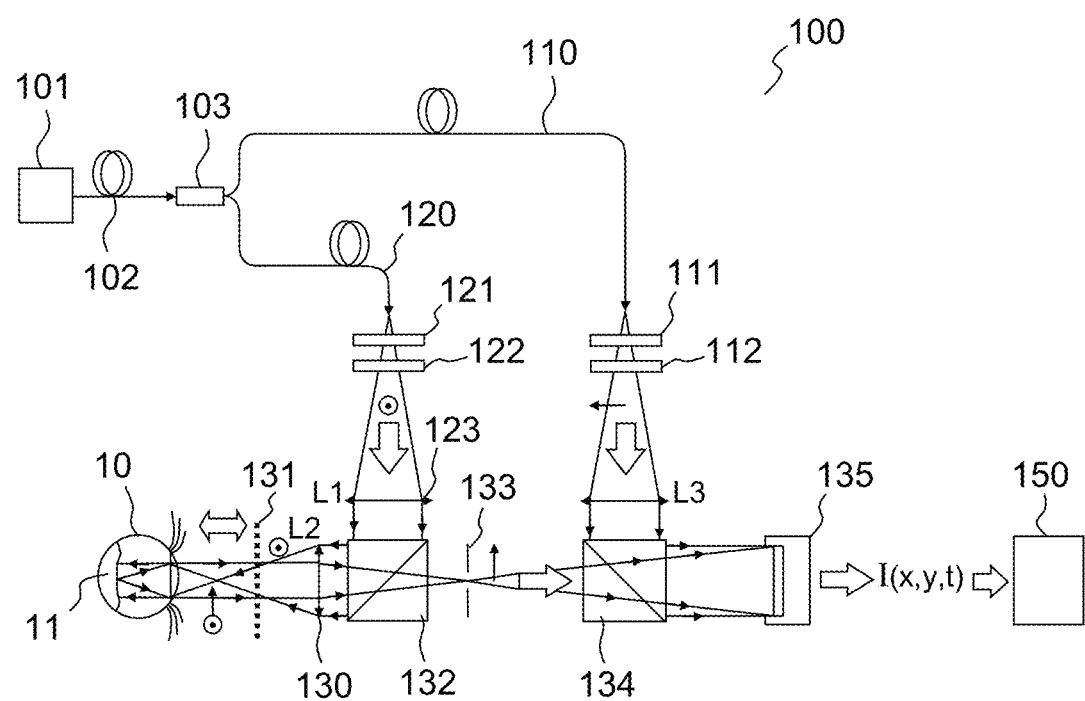
FIG. 1, a diagram of an exemplary laser Doppler holography device according to the present disclosure.

FIG. 1 shows an exemplary laser Doppler holography device 100 providing the interferograms whose processing is an object of the present disclosure.

Figure 2:
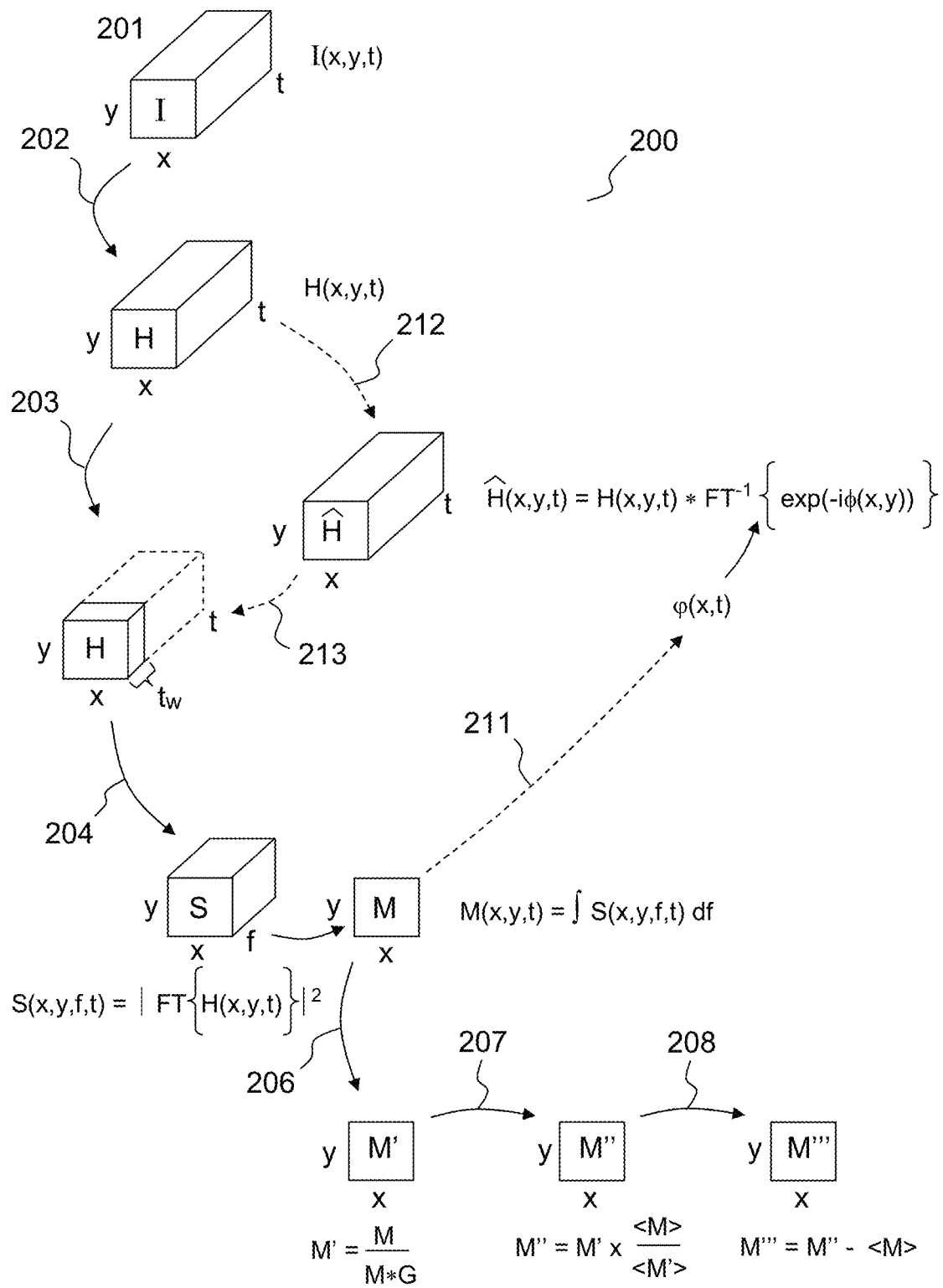
FIG. 2, a diagram illustrating processing steps in an exemplary method according to the present disclosure.

FIG. 2 relates to processing steps of a method according to an embodiment of the present disclosure.

The device 100 comprises an interferometer, for example, as illustrated in FIG. 1, a fibered Mach-Zehnder optical interferometer in the on-axis configuration. A source beam 102 emitted by a temporally coherent optical source 101 of optical frequency $f_0$ (for example a laser) is sent to a dividing optical element 103 (for example a fibered optical coupler) and divided between an illumination beam 120, $E_{obj}$, and a reference beam 110, $E_{LO}$. The illumination beam 120, $E_{obj}$, is directed towards a layer 11 of the eye 10, after passing through a waveplate 121, a linear polarizer 122, a first optical lens 123, being reflected off a beamsplitter 132, and passing through a second optical lens 130. After illuminating the layer 11, a portion of the light is backscattered to an optical sensor 135 (i.e. a two-dimensional optoelectronic detector) after passing through the second optical lens 130, the beamsplitter 132, and a combining element 134, for example a non-polarizing beamsplitter. The reference beam, $E_{LO}$, is directed to the optical sensor 135 following an optical path comprising a waveplate 111, a linear polarizer 112, a third optical lens 113, and the combining element 134. The data obtained from the optical sensor 135 are sent to a processing unit 150 that processes the data according to the method of the present disclosure, for example a method comprising the steps described in FIG. 2.

Generally, the processing unit 150 according to the present disclosure can comprise one or further physical units, for example one or further computers. When in the present disclosure, it is referred to calculation steps or processing steps for the implementation of methods, it is implied that each calculation step or processing step can be implemented by software, hardware, firmware, microcode, or any appropriate combination of these technologies. When a software is used, each calculation step or processing step can be implemented by instructions from a computer program or a software code. These instructions can be stored or transmitted to a storage medium read by the processing unit and/or be executed by the processing unit in order to implement the processing or calculation steps.

According to an example of the device 100, the part of the layer 11 of the eye 10 that can be imaged (the field of view) is fixed and depends on the parameters of the optical system that is used (comprising lens vergence, distance between lenses, distance between the eye 10 and the second lens 130 and distance between the sensor 135 and the third lens 113). The applicant demonstrated that it is possible to obtain a configuration with a variable field of view and, in particular, a larger field of view, by adding an optical element 131 (for example, an additional retractable lens) between the eye 10 and the second lens 130. This element is retractable and its action can therefore be enabled or disabled without disturbing the configuration of the instrument because any change of optical conjugation can be compensated for by a numerical holographic propagation.

According to a particular embodiment of the present disclosure, the optical source 101 is a fibered single-mode external cavity diode laser. The optical source is, for example, configured to emit light in the infrared domain. The power of the light from the illuminating beam that is reaching the eye 10 is compliant with the exposure levels of the international standard for ophthalmic instruments.

For example, the optical sensor 135 is a camera with a frame rate that is inferior to a given low frame rate value, for example about 10 kHz. In the present disclosure, such a camera is referred to as a "slow camera".

According to another example, the optical sensor 135 is a camera with a frame rate that is superior to said low frame rate value. In the present disclosure, such a camera is referred to as a "fast camera".

An electric field of the reference beam can be written $E_{LO}(t)=A_0 e^{i2\pi f_0 t}$; where $A_0$ is a complex amplitude of the reference beam. An electric field of the backscattered beam can be written $E(t)=A(t) \cdot e^{i2\pi f_0 t}$; where A(t) is the complex amplitude that contains the information resulting from the interaction between the illumination beam, $E_{obj}$, and the moving scatterers in the layer 11 under study. A moving scatterer in the layer 11 under study, typically a red blood cell, reflects light from the illuminating beam and induces a shift in the optical frequency of this light that depends on the velocity of the scatterer (the blood flow). The large distribution of velocity of the scatterers in a biological object leads to a large frequency content in the backscattered beam, referred to as the optical Doppler power spectrum in the present disclosure. Therefore, the optical Doppler power spectrum is the parameter carrying information on blood flows that requires to be extracted for blood flow imaging.

Figure 3A:
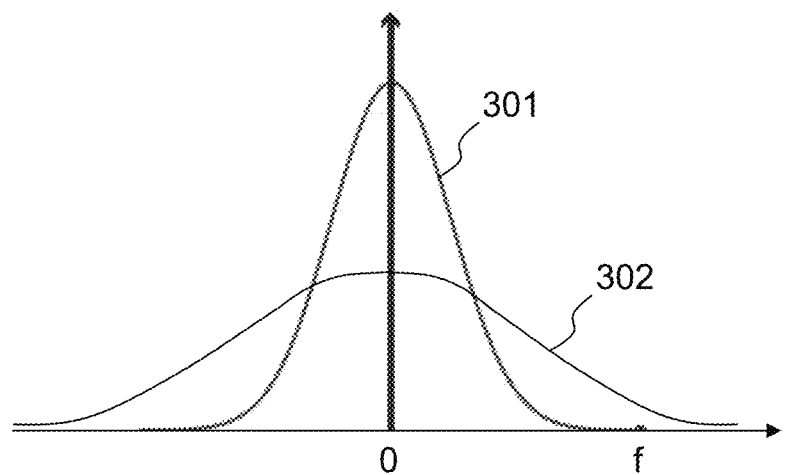
FIG. 3A to 3C, schematics illustrating the optical Doppler power spectrum (3A) for different flows and the calculation of a Doppler image via integration of the Doppler power spectrum wherein a two-dimensional optoelectronic detector with a large frame rate $f_{s1}$ (3B) and a low frame rate $f_{s2}$ (3C) is used.

A schematic view of an exemplary optical Doppler power spectrum is shown in FIG. 3A. The optical Doppler power spectrum is a particular function of the frequency shift with respect to the optical frequency of optical source with a width determined by the characteristics of the flows that are present in the layer 11. The dominant presence of low flows corresponds to an optical Doppler power spectrum 301 that is rapidly decreasing with increasing frequencies. The dominant presence of high flows corresponds to an optical Doppler power spectrum 302 that is slowly decaying with increasing frequencies. The optical Doppler power spectrum can follow a Gaussian law with a mean equal to the optical frequency of the laser and a standard deviation proportional to the magnitude of the flow in the layer 11.

The applicant showed that it is possible to estimate the optical Doppler power spectrum by detecting (with the optical sensor 135) and processing (with the processing unit 150) the two-dimensional interference pattern resulting from the interference between the colinear backscattered and reference beam (E and $E_{LO}$). In the present disclosure, the acquisition of the two-dimensional interference pattern by the optical sensor will be referred to as an interferogram I(x,y,t).

The interferogram I(x,y,t) produced by the optical sensor is $I=|E+E_{LO}|^2$, it is a two-dimensional matrix of real values, defined by a number of pixels along two dimensions of the optical sensor, defined in a plane substantially orthogonal to the direction of the reference beam. The pixels can be identified using coordinates along the two dimensions. The coordinates will be referred to as x and y in the present disclosure. The number of pixels depends on the specifications of the optical sensor 135. The interferograms are acquired over time with the optical sensor 135 so that I(x,y,t) is also a function of time t.

One object of the present disclosure is the processing of the interferograms in the processing unit 150 to generate a movie of the blood flow in a field of view of a layer 11 of the eye 10.

A processing method of an embodiment of the present disclosure is shown in FIG. 2. The interferograms are acquired over time (step 201) and for each interferogram I(x,y,t), a corresponding hologram H(x,y,t) is reconstructed (step 202), for example by angular spectrum propagation of the recorded interferogram via Fresnel transform, as disclosed in Goodman, *Introduction to Fourier optics*. Roberts and Company Publishers (2005). Thus, for each interferogram, it is possible to obtain a hologram with complex values H(x,y,t)=Fresnel{I(x,y,t)} in a field of view of a plane of the layer 11. The field of view is a few mm$^2$, typically a square of 4 mm by 4 mm. The reconstruction distance is large enough so that the holographic twin parasitic image energy is spread over the reconstructed hologram and has no appreciable effect on the resulting image.

A certain number N of consecutive holograms, typically between a few hundreds and a few thousands, calculated over a time window $t_w=N/f_s$ is selected (step 203) from the stream of holograms (calculated from the stream of detected interferograms). The choice of the parameter $t_w$ determines the temporal resolution of the device according to the present disclosure. In order to have a trade-off between temporal resolution and signal-to-noise ratio, a time window between 0.5 and 20 ms, advantageously between 1 and 20 ms can be used. As an example, when the optical sensor is a fast camera with a frame rate of 75 kHz, a time window of 6.8 ms can be used, meaning that 512 holograms are selected.

The applicant showed that it is possible to calculate (step 204) a squared norm of a time-frequency Fourier transform of the complex amplitude of the N holograms, in order to obtain an estimate of the optical Doppler power spectrum. In the present disclosure, said estimate of the optical Doppler power spectrum, will be simply referred to as "Doppler power spectrum" S(x,y,t,f). Mathematically, the step 204 can be written:

$$S(x,y,t,f) = |\int_{t}^{t+t_w} H(x,y,\tau) e^{-2i\pi f\tau} d\tau|^2$$

The Doppler power spectrum is expressed as a function of a frequency, f, referred to as Doppler frequency and centered around the zero frequency.

The calculation (step 204) of the Doppler power spectrum may be performed in a sliding manner, meaning that the N consecutive holograms on which is performed the time-frequency Fourier transform are constantly changing over time. Each time when a new quantity of holograms is added to the N holograms, the same quantity of hologram is removed from the N holograms and the Doppler power spectrum is calculated on a number N of holograms of a different composition. A certain overlap can be defined between successive number N of holograms, said overlap being comprised between 0 and N−1. For example, an overlap of N/2 images can be chosen meaning that two successive Doppler power spectra are calculated over quantities of holograms sharing half of the same content. An overlap of zero images can also be chosen, meaning that two successive Doppler power spectra are calculated over different holograms. A large overlap, for example N−1, can improve the temporal resolution of the Doppler images but typically increases the calculation time.

For each time window, $t_w$, corresponding to N holograms, an image M(x,y,t), called Doppler image, can be calculated by performing an integration (step 205) of the Doppler power spectrum over a selected range of Doppler frequencies [$f_1$, $f_2$], chosen in order to reveal specific features in the layer 11.

Figure 3B:
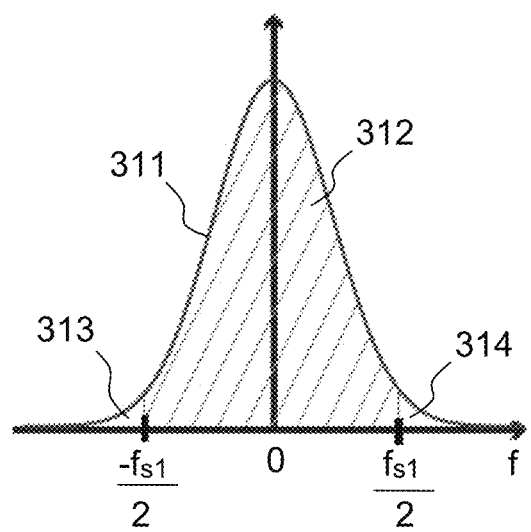

FIG. 3B illustrates an example of calculation (step 205) of the Doppler image by integration of the Doppler power spectrum 311 over a large range of Doppler frequencies. The range of Doppler frequencies encompasses a major part 312 of the Doppler power spectrum 311, only minor parts 313 and 314 of the Doppler power spectrum 311 are left out. This is the typical case encountered when the optical sensor 135 is a fast camera with a frame rate $f_{s1}$ that is close or superior to half of the largest Doppler frequencies produced by the moving scatterers in the layer 11. In the case of said fast camera, the Nyquist-Shannon criteria is verified and the signal corresponding to those frequencies is not aliased and clearly visible. Typically, the highest Doppler frequencies in the ocular image being 30 kHz (originating from arteries), the sensor frame rate needs to be superior or equal to 60 kHz.

Figure 3C:
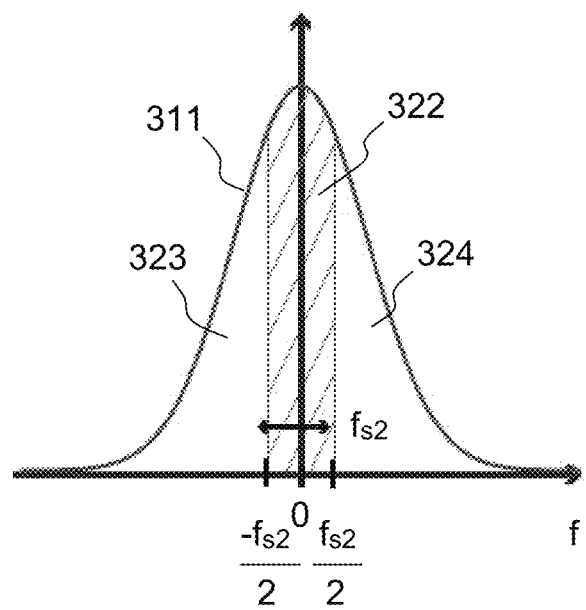

Alternatively, a particular embodiment of the invention comprises the use of a slow camera to record the interferograms with a frame rate $f_{s2}$ that can be significantly inferior to twice the largest Doppler frequencies due to the moving scatterers in the layer 11, for example below about 10 kHz. As depicted in FIG. 3C, in such a configuration, the signals 323-324 corresponding to frequencies above half of the frame rate of the camera are lost and the integration 205 of the Doppler power spectrum 321 over those frequencies may not be possible. The integration 205 of the Doppler power spectrum 321 is then limited to a narrow area 322 and the information contained in the areas 323-324 may be lost. The information contained in the narrow area 322 is mostly related to low flows (scatterers that are producing a small Doppler frequency shift of the light of the illuminating beam).

The integration (step 205) can be written mathematically as:

$$M(x,y,t) = \int_{f_1}^{f_2} S(x,y,t,f) df + \int_{-f_2}^{-f_1} S(x,y,t,f) df$$

where $f_1$ and $f_2$ define a frequency range over which is integrated the Doppler power spectrum to calculate the Doppler image.

FIG. 4A-4D show experimental Doppler images of a retina obtained with different methods. The experimental images are obtained using a device as shown in FIG. 1, where the source is a single wavelength laser diode emitting 45 mW of light at 785 nm, and the optical sensor is a fast CMOS camera with a frame rate of 75 kHz.

FIG. 4A and FIG. 4B show Doppler image obtained by integration of the Doppler power spectrum over different ranges of Doppler frequencies. FIG. 4C shows the composite Doppler image that it is possible to obtain from FIG. 4A and FIG. 4B in order to reveal the types of blood vessels in the layer 11. The applicant has shown that the type of blood vessels that are revealed is determined by the selective frequency filtering range used to compute the power Doppler image. In particular large Doppler frequencies (typically 6-30 kHz) correspond to signal originating from vessels with high flows, while lower Doppler frequencies (typically 2.5-6 kHz) correspond to signal originating from vessels with lower flows. The applicant demonstrated that when calculating separately the Doppler images (FIG. 4A-4B) corresponding to the low and high Doppler frequencies and combining them into a single composite color image (FIG. 4C), it is possible to simultaneously display vessels with a wide range of flows and qualitatively encode the flow information in the image color, leading to the clear discrimination of blood vessels according to their flows, as can be seen in FIG. 4C. This particular embodiment of the device and method in the present disclosure can be used, for example, to distinguish ocular arteries from ocular veins and presents an advantage over other techniques like ICGA, as illustrated in FIG. 4D which shows an image of the same layer 11 as in FIG. 4A-4C but obtained with the ICGA technique. In particular, a large ocular artery visible is in FIG. 4C and FIG. 4D (obtained with the present method) but is not revealed by the ICGA technique (as shown in FIG. 4D.

Apart from the Doppler power spectrum analysis as such, it may be of clinical interest to further increase the resolution of the Doppler images of ocular blood flows obtained by the method presented above. As a matter of fact, the quality of the Doppler images obtained after steps 201-205 can be undermined by several factors such as global movement of the eye 10 or imperfect optical system.

The applicant showed that the quality of the Doppler images can be significantly improved by the processing steps 206-208.

Figure 5A:
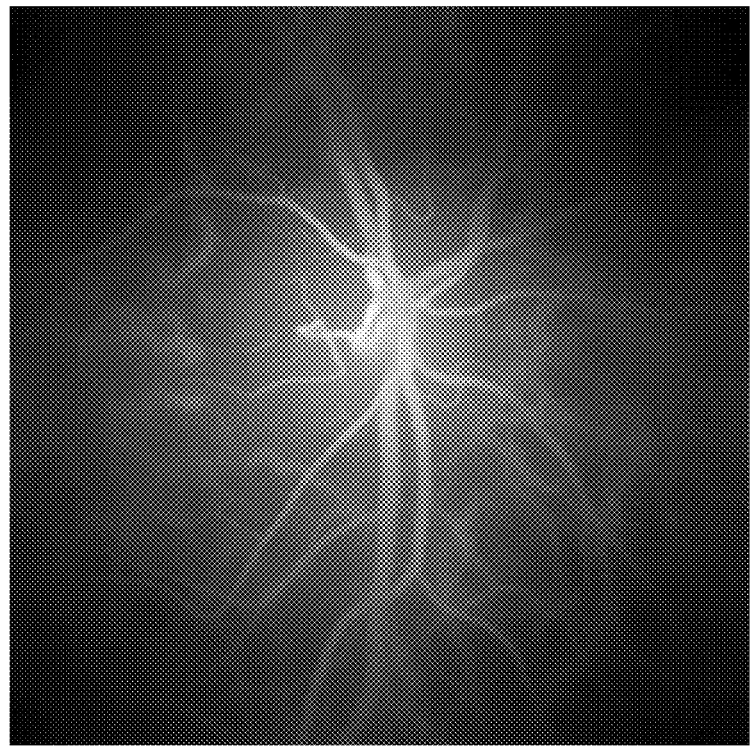
FIGS. 5A and 5B, pictures showing a Doppler image (5A) and a corrected Doppler image (5B) obtained with a device of the example of FIG. 1.

FIG. 5A shows a Doppler image with a lateral shading toward the margins, called "vignetting" in the present disclosure.

The applicant demonstrated that said vignetting can be corrected for by applying a particular procedure (step 206) to the Doppler image, wherein the Doppler image, M, is divided by a version of itself that has been convoluted with a Gaussian function in order to become blurry. Said procedure (step 206) results in a "devignetted" image, M', that can be written as:

$$M' = \frac{M}{M * G}$$

where the symbol "*" denotes the convolution operator, and G denotes a Gaussian function. Details on a devignetting method applied in another context and an exemplary Gaussian function can be found, for example, in Leong et al. "*Correction of uneven illumination (vignetting) in digital microscopy images.*" Journal of clinical pathology 56.8 (2003): 619-621.

Figure 5B:
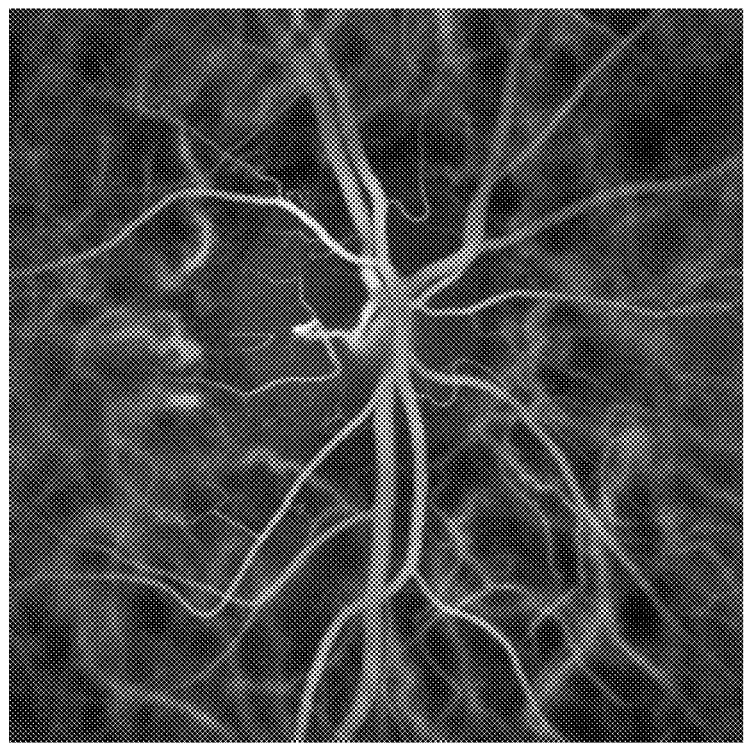

As shown in FIG. 5B, by virtue of the devignetting procedure (step 206) to the image in FIG. 5A, the vignetting is no more present in the image, and blood flows in the edges of the image are revealed.

FIGS. 5A and 5B have been obtained using a device as shown in FIG. 1, where the source is a single wavelength laser diode emitting 45 mW of light at 785 nm, and the optical sensor is a fast CMOS camera with a frame rate of 75 kHz.

The applicant showed that the devignetted Doppler image can be further improved by combining a normalization procedure (step 207) with a baseline subtraction procedure (step 208).

The normalization procedure may be performed over the devignetted Doppler image, M', resulting in a normalized Doppler image, M". Mathematically, said normalization procedure (step 207) can be written as:

$$M'' = \frac{A}{A'} M'$$

where A= $\langle$ M(x,y) $\rangle$ and A'= $\langle$ M'(x,y) $\rangle$, are the mean intensities (i.e. the average of the intensity of all pixels over the two dimensions x and y) of the Doppler image and the devignetted Doppler image, respectively.

The baseline subtraction procedure (step 208), can be written M'''=M"−A, and results in an image M''' that will be referred to as the corrected Doppler image in the present disclosure. Said procedure corresponds to the subtraction of the mean intensity, A, of the Doppler image, M, from the normalized Doppler image, M".

The applicant showed that, by virtue of said procedures (step 207-208), the corrected Doppler image M''' provides ocular blood flow data in which the various parasitic contributions from the motion of the eye and the imperfect optical system are significantly reduced.

Note that the reduction in the parasitic contributions is obtained thanks to the synergic effects of the baseline subtraction (step 208) with the normalization procedure 207 in which the spatial distribution of the intensity in the image is changed while the mean intensity is conserved.

The applicant showed that, after the step 208, the corrected images M''' acquired during a certain amount of time can be assembled to generate a movie of ocular blood flows which is of high quality and useful for the investigation of temporal waveform of the flows (or pulsatile flows) in the vessels of the layer 11. For example, it allows for the monitoring of the systolic and diastolic pulsatile flows in the veins and arteries of the retina or choroid.

Figure 6A:
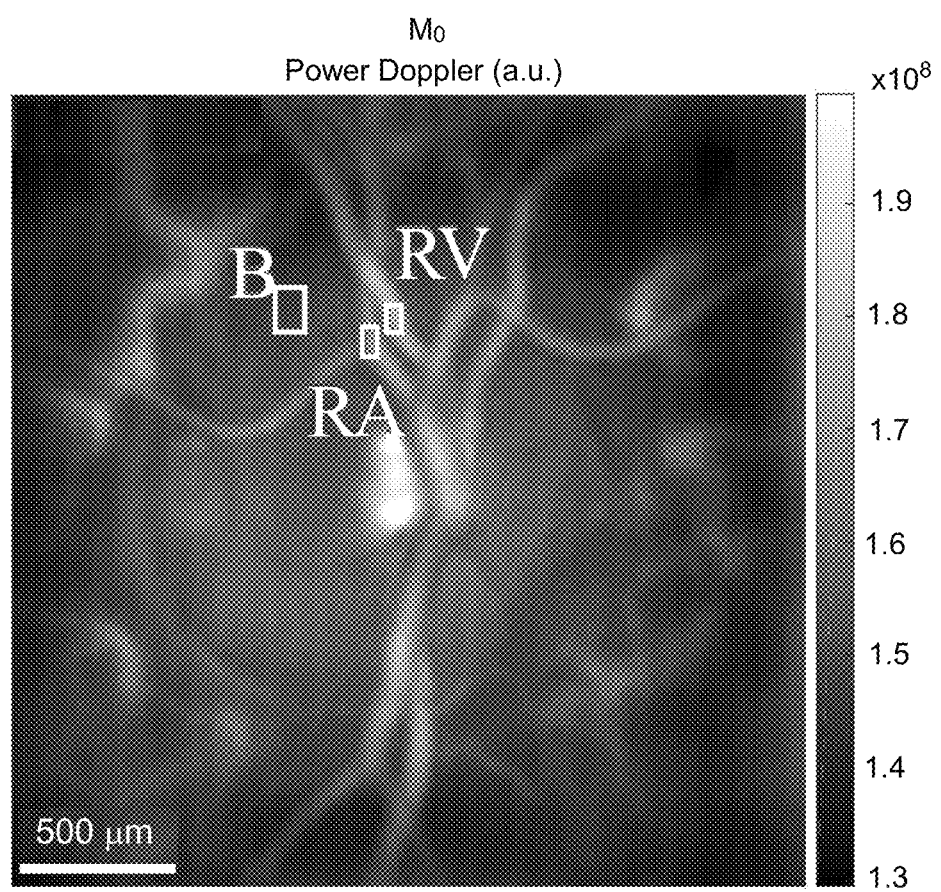
FIG. 6A, a Doppler image of the posterior layers of the eye specifying different regions of interest (B: background, RV: retinal veins, RA: retinal arteries)
Figure 6B:
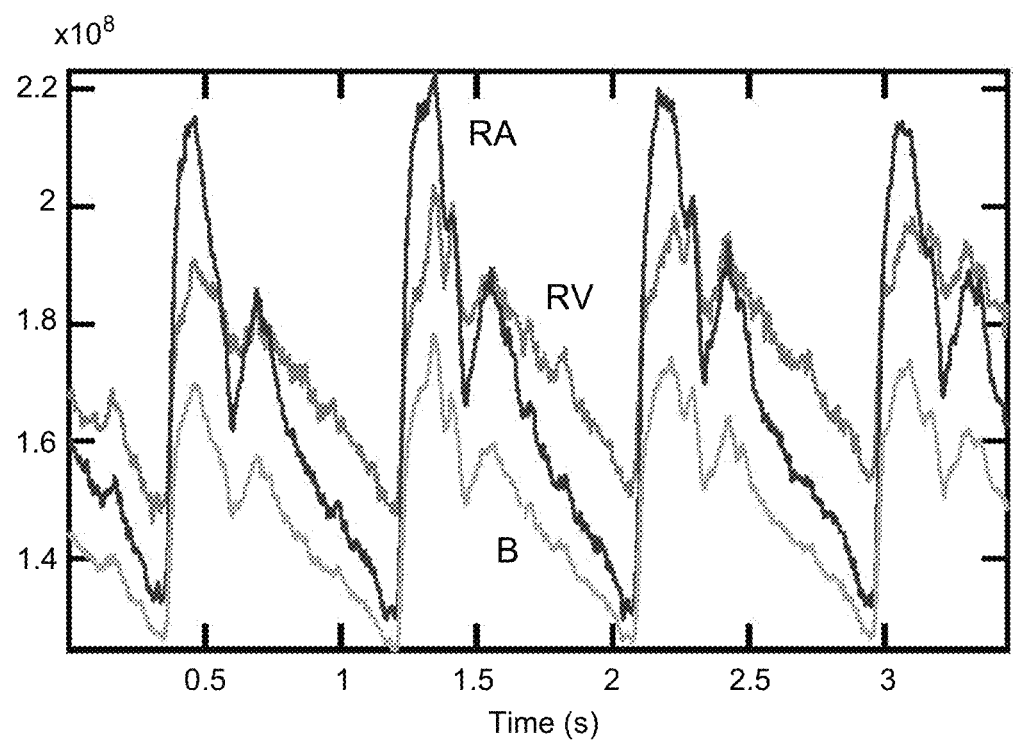
FIGS. 6B and 6C, temporal evolution of ocular blood flows for the different regions of interest in said Doppler image, before (6B), and after (6C) subtraction of the baseline in the normalized Doppler image according to the present disclosure.

FIG. 6A-6B illustrate the technical effect of the procedures 207-208 when imaging ocular blood flows of a layer 11 of the eye 10.

FIG. 6A is an experimental Doppler image of a retina, in which three regions of interest are indicated (RA, RV, and B). Such experimental image is obtained using a device as shown in FIG. 1, where the source is a single wavelength laser diode emitting 45 mW of light at 785 nm, and the optical sensor is a fast CMOS camera with a frame rate of 75 kHz.

Figure 6C:
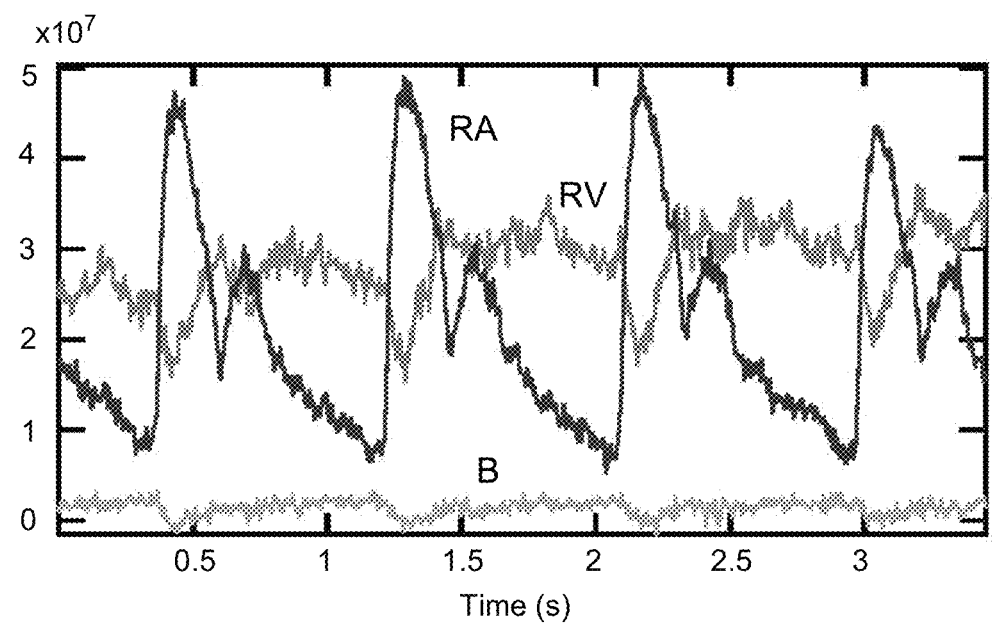

FIG. 6B shows graphs of a temporal evolution of blood flows for the three regions of three regions of interest of the Doppler image in FIG. 6A. FIG. 6C shows a graph of a temporal evolution of blood flows for the same three regions of interest but taken from a corrected image M''' (obtained after applying the procedures 207-208) to the Doppler image of FIG. 6A.). The temporal evolutions are obtained after assembling several consecutive Doppler images taken over time to generate a movie and extracting blood flow information from this movie. Without the procedures 207-208, temporal evolutions of blood flows in the three regions of interest have similar shapes so that the type of features present in each region of interest cannot be easily distinguished. On the contrary, with the procedures 207-208, different trends of temporal evolutions are revealed.

Therefore, it is demonstrated that the normalization procedure (step 207) and subtraction of the baseline signal (step 208) in the Doppler images constituting the movie as in the present disclosure reveals flow behaviors specific to the probed features in the Doppler image and, for example, provide a way to identify pulsatile flows of retinal arteries and retinal veins and distinguish them from the background.

Moreover the applicant showed that blood flows in the vessels of the ocular layer 11 imaged using a method according to the present disclosure can be quantified linearly in arbitrary units, and encoded in the value of each pixel of the corrected image. This can provide information on rheologic parameters of the ocular vessels that scale with the blood flow (such a viscosity, elasticity and pressure field) and are useful for diagnosing eye-related diseases and other type of diseases (for example, hypertension).

In an optional embodiment of the present disclosure, an additional processing step can be made before the calculation 204 of the Doppler power spectrum, to dissociate the useful blood flow signal from a signal resulting from motion of eye tissues. Such processing step provide images with significantly enhanced resolution The applicant demonstrated that this increase in resolution is especially significant when Doppler spectra are integrated over a low frequency range, typically frequencies below about 5 kHz.

Such additional processing step comprises a singular value decomposition (SVD) of each second plurality of holograms H(x,y,t) acquired over a time window $t_w$.

Figure 7:
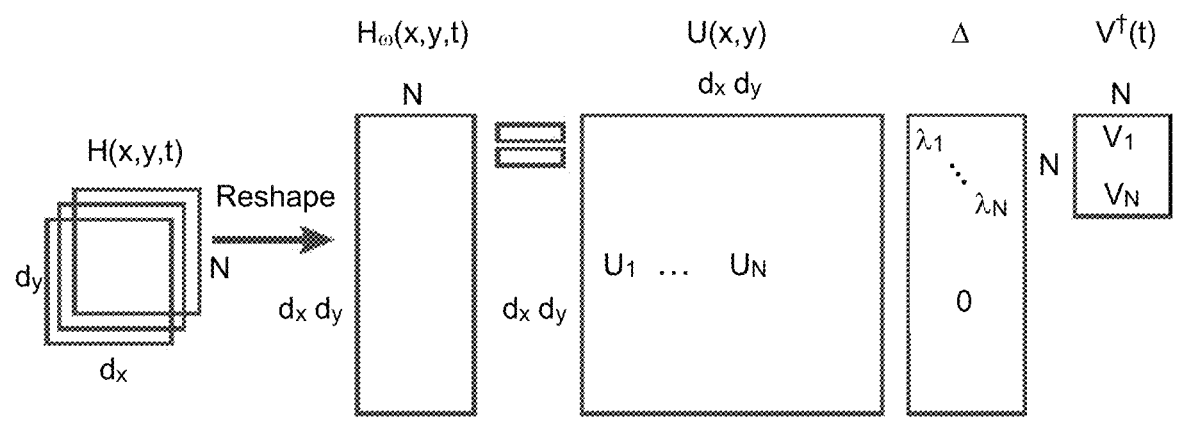
FIG. 7, a diagram illustrating the processing steps of the singular value decomposition (SVD) procedure according to an embodiment of the present disclosure.

FIG. 7 illustrates an array operation that can be used to perform such singular value decomposition of each second plurality of holograms.

In an embodiment of the present disclosure, the SVD of a second plurality of N holograms H(x,y,t), arranged in a 3D array of size (dx, dy, N), comprises two steps. First, the 3D array of the plurality of N holograms H(x,y,t) is reshaped in a 2D matrix, $H_w(x,y,t)$ of size (dx, dy, N), by concatenating the two spatial dimensions in a single one, as depicted in FIG. 7. Second, the 2D matrix is decomposed in singular values according the following formula:

$$H_w = U \Delta V^\dagger$$

U and V are unitary matrices of dimensions (dx, dy, dx, dy) and (N,N) whose columns correspond to the spatial and temporal eigenvectors (singular vectors), respectively. The † superscript denotes the conjugate transpose operator. Δ is a non-square diagonal matrix of dimension (dx, dy, N). The diagonal terms in Δ are the singular values ($\lambda_1, \ldots, \lambda_N$) of the matrix $H_w$.

Any coefficient of the matrix $H_w$ can then be expressed as follows:

$$H_w(x, y, t) = \sum_{i=1}^{N} \lambda_i U_i(x, y) V_i(t)$$

The SVD decomposes a matrix in two sub-spaces, a signal sub-space (characterized by significant correlations between its rows and/or columns) and a noise sub-space (characterized by low correlations between its rows and columns). The signal sub-space is associated with the largest singular values whereas the noise subspace is associated with the smaller singular values. Therefore, the SVD allows for filtering out the noise sub-space from the space containing both the contributions from signal and noise. Details on the SVD method applied in another context can be found, for example, in Baranger et al. "*Adaptive spatiotemporal SVD clutter filtering for ultrafast Doppler imaging using similarity of spatial singular vectors.*" IEEE transactions on medical imaging 37.7 (2018): 1574-1586.

Figure 8A:
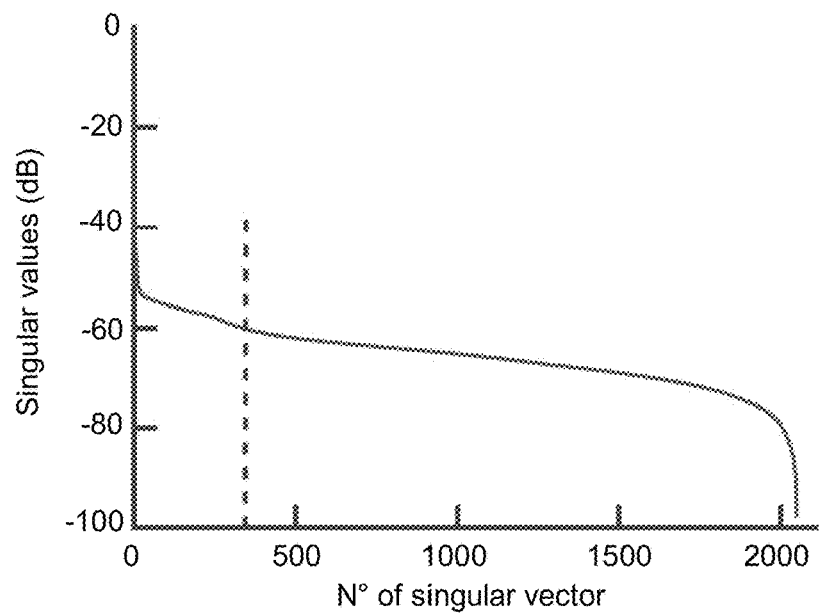
FIG. 8A, 8B illustrate the role of eigenvectors identified in the SVD according to an embodiment of the present disclosure.
Figure 8B:
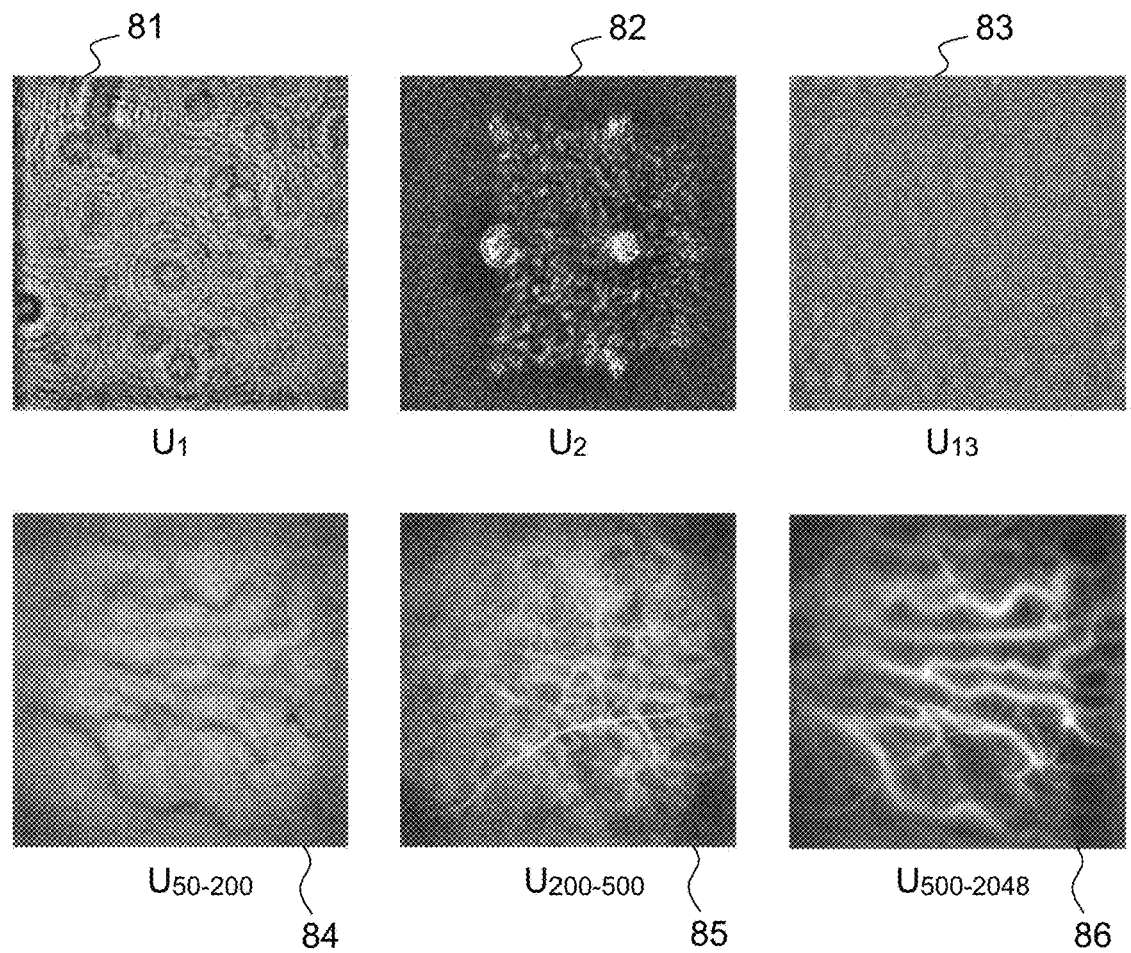

FIG. 8A-8B depicts an example of ordered normalized singular values in dB for a series of singular vectors found after applying the SVD procedure to a second plurality of holograms.

FIG. 8A-8B are experimental images obtained using a device as shown in FIG. 1, where the source is a single wavelength laser diode emitting 45 mW of light at 785 nm, and the optical sensor is a fast CMOS camera with a frame rate of 75 kHz.

As shown in FIG. 8A, the singular values decrease with increasing singular vector index. As shown in FIG. 8B, the first eigenvectors (81-83) contain parasitic information due to the motion of the eye tissues while the eigenvectors with a larger index (84-86) contain ocular blood flow data. The parasitic information from the bulk motion of tissues, technical noises, laser intensity fluctuations, and reflections from the anterior segment of the eye can then be filtered out by defining a noise matrix $H_{noise}$, containing the contribution from the largest singular values (i.e. the singular vectors with an index below a certain threshold illustrated by the dotted line in FIG. 8A), and subtracting it from $H_w$:

$$H_f = H_w - H_{noise}$$

This operation enables to retrieve a second plurality of filtered holograms, using $H_f$.

Figure 9:
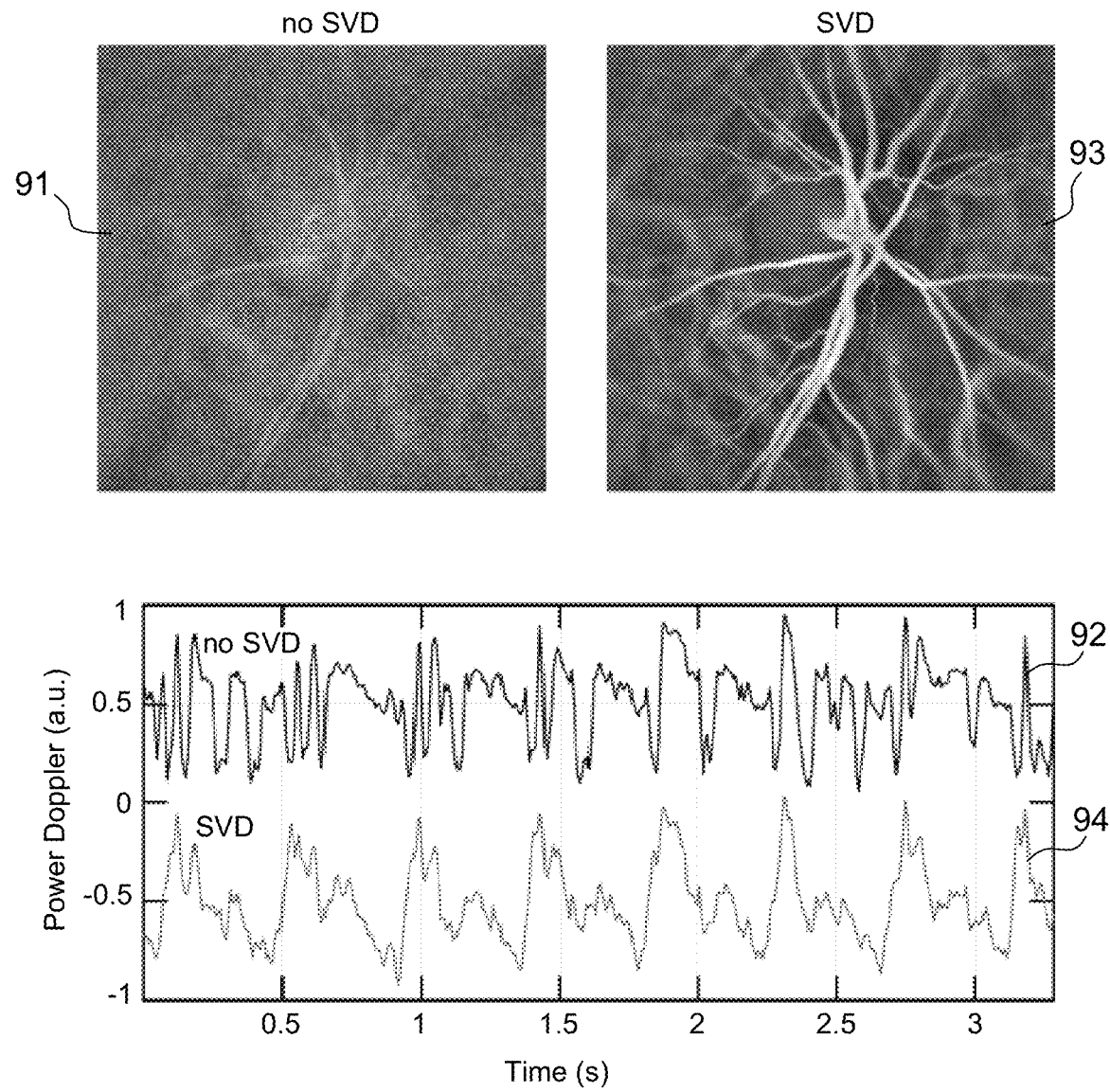
FIG. 9 shows Doppler images of a retina and temporal blood flow profiles before and after applying the SVD procedure.

FIG. 9 shows that after performing the steps 204 to 208 on said filtered holograms, it is possible to obtain a filtered Doppler image 93 of a superior quality in terms of spatial resolution compared to the corrected Doppler image 91 obtained only with the general algorithm 200 (i.e. without SVD).

Images 91 and 93 are experimental images obtained using a device as shown in FIG. 1, where the source is a single wavelength laser diode emitting 45 mW of light at 785 nm, and the optical sensor is a fast CMOS camera with a frame rate of 75 kHz.

The benefit of the SVD procedure is further visible when extracting temporal blood flow profiles from the movies generated from the sequential assembling of filtered Doppler images (with SVD) compared to corrected Doppler images (without SVD). With SVD, the temporal blood flow profile (94) is time-resolved and we can see the cardiac cycles whereas, without SVD, the temporal profile (92) has a lower signal to noise ratio and the cardiac cycles are hardly visible.

The enhancement is especially very effective for low blood flows corresponding to Doppler frequencies below 5 kHz where the signal from the background is particularly significant.

In an optional embodiment of the present disclosure, an additional processing step is made after the calculation of the corrected Doppler image, in which an opposite of the corrected Doppler image is calculated, i.e. an image with an inverted contrast with respect to the corrected Doppler image. Said opposite of the corrected Doppler image is referred to as an "opposite Doppler image", in the present disclosure.

Figure 10:
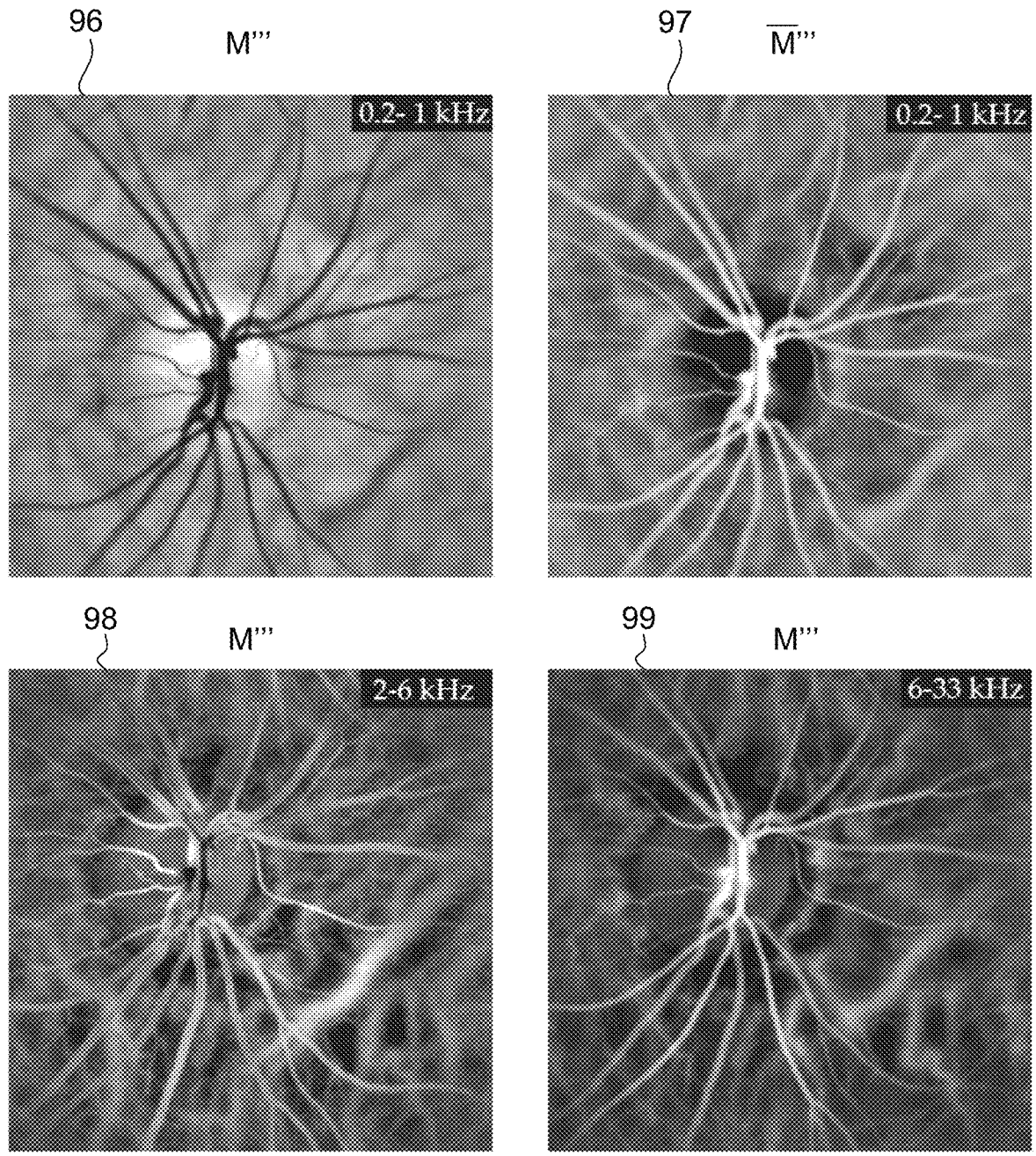
FIG. 10 shows three corrected Doppler images and an opposite Doppler image obtained from integration of a Doppler power spectrum over several ranges of frequencies.

FIG. 10 shows corrected Doppler images (96,98,99) generated from integration of a Doppler power spectrum over several ranges of frequencies, namely ([0.2-1 kHz], [2-6 kHz] and [6-33 kHz]) and an opposite Doppler image 97 obtained from an inversion of contrast of the corrected Doppler image 96 corresponding to the lowest frequencies. In particular, it can be seen that the opposite Doppler image 97 resembles the corrected Doppler image 99 obtained from integration of the Doppler power spectrum over high frequencies.

Such additional step comprises the calculation of an opposite of the corrected Doppler image M'''. Mathematically, this calculation can be written: $\overline{M'''} = -M'''$. Once several opposite Doppler images are calculated they are sequentially assembled to generated a movie, revealing temporal behaviors of high flow levels.

Especially, such additional step allows for retrieving information on the high frequency content of the Doppler power spectrum by analyzing the low frequency content of the Doppler power spectrum. Such feature can be understood as originating from the deformation of the Doppler power spectrum due to a variation in the high flows. Indeed, changes in high flows will distort the shape of the Doppler power spectrum, and this distortion will be also visible near the center of the Doppler power spectrum. Typically, an increase in the high flows will enlarge the Doppler power spectrum and reduce its height (as visible in FIG. 3A), resulting in a decrease in the spectrum amplitude near the center. Consequently, by representing a movie of the opposite Doppler images calculated over a low frequency range, it is possible to obtain information on high flows.

The applicant showed that this additional step is especially advantageous in a case where a slow camera is used to detect the interferograms.

Advantageously, this additional step can be combined with the SVD procedure in order to obtain ocular blood flow profiles with an enhanced resolution.

In addition to what is described above, the presence of refractive aberrations in the optics of the eye 10 can corrupt the formation of Doppler image and limit the information on ocular blood flows that can be extracted from said image. In order to solve this technical problem, the applicant demonstrated the feasibility of correcting for the refractive aberrations introduced by the imperfections of the eye 10 by applying a digital aberration compensation algorithm to the holograms (H(x,y,t)).

This operation, referred to as "rephasing" comprises: first, the estimation 211, from the Doppler image M, of the refractive aberrations of the eye in terms of a phase mask, ϕ(x,y), that can be expressed as a linear combination of Zernike polynomials, second, the correction 212 of the hologram H, by applying the inverted said phase term 220 according to the following formula:

$$\hat{H}(x,y,t) = H(x,y,t) * FT^{-1}\{\exp(-i\phi(x,y))\}$$

where $FT^{-1}$ denotes the inverse spatial Fourier transform. This results in a plurality of compensated holograms $\hat{H}(x,y,t)$.

Subsequently to 212, a selection 213 of a certain number N of compensated holograms is made (similarly to the selection 203). Then, the same procedures as described before 204-208 are applied in order to obtain the corrected image M'''. This aberration compensation technique improves significantly the quality of the corrected images in terms of spatial resolution.

In a possible embodiment of the present disclosure, the phase term is estimated iteratively by convergence of a particular metrics calculated over the Doppler image and the phase term is expressed as a linear combination of Zernike polynomials.

In another embodiment of the present disclosure, the estimation of the phase term is made from inter-correlation of Doppler images calculated using sub-apertures selected within the spatial Fourier transform of the holograms In possible embodiments of the present disclosure, the rephasing procedure can be done iteratively or non-iteratively, see Hillmann et al. "*Aberration-free volumetric high-speed imaging of in vivo retina.*" Scientific reports 6 (2016): 35209. and Ginner et al. "*Noniterative digital aberration correction for cellular resolution retinal optical coherence tomography in vivo*" Optica 4.8 (2017): 924-931.

According to a third aspect, the invention relates to a method for full-field blood flow imaging of ocular vessels in a field of view of at least a first layer of the eye, the method comprising the acquisition over time of at least two pluralities of interferograms of said at least first layer using a laser Doppler holography technique, wherein said at least two pluralities of interferograms are acquired at two different optical frequencies.

According to one or further embodiments, the method according to the third aspect further comprises:

for each plurality of interferograms of said at least two plurality of interferograms:

the calculation, for each interferogram of said plurality of interferograms, of a hologram, wherein the hologram is defined by a complex amplitude of a light beam backscattered by said at least first layer in a given spatial plane, resulting in a first plurality of holograms;

the selection, in sequential time windows, of second pluralities of holograms from said first plurality of holograms;

the calculation, for each said second plurality of holograms, of a Doppler power spectrum;

the calculation, based on said Doppler power spectrum, of at least a first Doppler image, thus generating at least a first plurality of Doppler images and a second plurality of Doppler images associated to each of said optical frequencies.

By virtue of said method, it is possible to generate Doppler images generated from acquisition of interferograms at at least two different optical frequencies and retrieve depth-resolved images of blood flows in the retina and the choroid. More specifically, it is possible to discriminate local optical absorption from blood flow, because the dependence of absorption of pigmented areas with the optical wavelength differs from the dependence of the blood flow signal with the optical wavelength.

According to one or further embodiments, the method according to the third aspect further comprises the sequential assembling of said Doppler images to generate a movie showing an evolution over time of blood flows in said ocular vessels.

It is understood that any of the embodiments of the method described according to the first aspect can be applied to the method according to the third aspect, for example, the processing of the Doppler images.

According to a fourth aspect, the present disclosure relates to a laser holography device configured to implement the method according to the third aspect.

For example, a device according to the fourth aspect comprises:

an optical source configured for the generation of an illuminating beam and a reference beam, wherein said illuminating beam is configured for illuminating said at least first layer;

a combining element configured for combining the said reference beam and a part of said illuminating beam that is backscattered from said at least first layer;

a two-dimensional optoelectronic detector with a given frame rate, configured to acquire a plurality of interferograms, wherein an interferogram is defined as the signal resulting from the interference between the said reference beam and the part of said illuminating beam that is backscattered from the said at least first layer;

a processing unit configured for processing said plurality of interferograms.

According to one or further embodiments, a frequency of the optical source can be changed between at least two frequencies.

According to one or further embodiments, the change in the optical source frequency can, for example, be performed by switching or sweeping the frequency over time. For example, if the frequency of the optical source is switched between two frequencies, two interleaved pluralities of interferograms can be obtained, each corresponding to one of said frequencies. Each plurality of interferograms is then processed independently according to the present disclosure, resulting in two pluralities of Doppler images. Linear combination of the Doppler images of said pluralities of Doppler images can then be made, making it possible to obtain spectroscopic information on the ocular blood vessels present in said field of view. Especially in the case of the use of a slow camera, by virtue of this method, it is possible to discriminate local optical absorption from blood flow, because the dependence of absorption of pigmented areas with the optical wavelength differs from the dependence of the blood flow signal with the optical wavelength.

According to one or further embodiments of the present disclosure, it is moreover possible to achieve the measurement of both a local light absorption spectra, and a "2-depth sectioning" of ocular blood flows in retinal and choroidal layers by introduction of wavelength diversity of the optical source while acquiring and processing the interferograms as described before.

The change in the optical source (101) frequency can, for example, be performed by switching, changing, or sweeping the wavelength over time (and hence the optical frequency, as the wavelength is related to the optical frequency by the relation $\lambda=c/f$, where c is the speed of light in vacuum). A swept-source laser can be used as an optical source for this purpose. Typically, a source with an optical wavelength tuning range of about 50 nm, from about 820 nm to about 870 nm, and a sweep speed range of about 100000 nm/s or greater can be used.

If the optical source wavelength is switched repetitively between two or more values $(\lambda_1, \lambda_2, \ldots, \lambda_m)$, m series of interferograms are formed over time, among which:

a first series of interferograms, $I_1(x,y,t)$, formed when the wavelength of the laser is $\lambda_1$;

a second series of interferograms, $I_2(x,y,t)$, formed when the wavelength of the laser is $\lambda_2$; and, a m-th series of interferograms, $I_m(x,y,t)$, is formed when the frequency of the laser is $\lambda_m$.

The data may be organized according to one of the following methods.

In a first method, successive interferograms at given laser wavelengths ($\lambda_1, \ldots, \lambda_m$) can be processed by the algorithms (200) as described before, independently for each wavelength, resulting in m series of corrected Doppler images (($M_1'''$), ($M_2'''$), ..., and ($M_m'''$)). A linear combination of the corrected Doppler images can be calculated in order to obtain images representing a mix between absorption spectrum information and ocular blood flows, from which local absorption and ocular blood flows can be discriminated according to their respective variation against wavelength.

In a second method, successive interferograms can be processed by algorithms (200) as described before except that the hologram reconstruction (step 202) is modified by addition of a temporal Fourier transformation, over the time of each sweep (i.e corresponding to the wavelength $\lambda_1$, $\lambda_2, \ldots, \lambda_m$ in order to get a depth-resolved structural image of the retinal layers. This creates a plurality of holograms at depths $z_1, z_2, \ldots, z_m$. The series of depths $z_1, z_2, \ldots, z_m$ scales up linearly with the series of temporal Fourier frequencies when the wavelength sweep is done by linear detuning of the optical frequency with time. The resulting successive holograms for each depth, $H(x,y,t)$, can be processed independently following the steps 203-208 as described before, resulting in m depth-resolved Doppler images: $M'''(z_1), M'''(z_2), \ldots, M'''(z_m)$. Advantageously, "opposite Doppler images" $\overline{M}'''(z_1), \overline{M}'''(z_2), \ldots \overline{M}'''(z_m)$, can be calculated to reveal blood flows.

Although described though a number of detailed exemplary embodiments, the methods and devices according to the present disclosure comprise different alternative embodiments, modifications and improvements which will be obvious to those skilled in the art, it being understood that these different alternative embodiments, modifications and improvements fall within the scope of the invention as defined in the following claims.

The invention claimed is:

1. A method for full-field blood flow imaging of ocular vessels in a field of view of at least a first layer of the eye, the method comprising:
   the acquisition over time of a plurality of interferograms of said at least first layer using a laser Doppler holography technique, wherein said at least first layer is illuminated by a light beam;
   the calculation, for each interferogram of said plurality of interferograms, of a hologram wherein the hologram is defined by a complex amplitude of a light beam backscattered by said at least first layer in a given spatial plane, resulting in a first plurality of holograms;
   the selection, in sequential time windows, of second pluralities of holograms from said first plurality of holograms;
   the calculation, for each said second plurality of holograms, of a Doppler power spectrum;
   the calculation, based on said Doppler power spectrum, of at least a first Doppler image, thus generating at least a first plurality of Doppler images associated with said plurality of sequential time windows;
   the processing of each first Doppler image, wherein said processing comprises:

the devignetting of said first Doppler image, resulting in a devignetted first Doppler image;
   the normalization of said devignetted first Doppler image based on a spatial average of an intensity of said first Doppler image, resulting in a normalized first Doppler image;
   the subtraction, from said normalized first Doppler image, of said spatial average of said intensity of said first Doppler image, resulting in a corrected first Doppler image; and,
   the sequential assembling of said corrected first Doppler images to generate a movie showing an evolution over time of blood flows in said ocular vessels.

2. The method as claimed in claim 1, wherein the calculation, for each said second plurality of holograms, of a Doppler power spectrum, comprises:
   the calculation of a temporal Fourier transform of said second plurality of holograms; and,
   the calculation of the square of the norm of said temporal Fourier transform.

3. The method as claimed in claim 1, further comprising:
   a singular value decomposition of a 2D matrix generated from said second plurality of holograms resulting in a plurality of singular values and singular vectors;
   the filtering of said second plurality of holograms, using said plurality of singular values and singular vectors, resulting in a filtered plurality of holograms; and,
   wherein the calculation of said Doppler power spectrum is made on said filtered plurality of holograms.

4. The method as claimed in claim 1, wherein said calculation of each first Doppler image of the plurality of first Doppler images comprises the integration of said Doppler power spectrum over at least a first frequency range.

5. The method as claimed in claim 4, further comprising:
   the integration of said Doppler power spectrum over at least a second frequency range different from said first frequency range to generate at least a second Doppler image, thus generating at least a plurality of second Doppler images.

6. The method as claimed in claim 1,
   wherein said processing of each first Doppler image further comprises calculating the opposite of each corrected first Doppler image, and
   wherein said movie is generated from the sequential assembling of said opposite of said corrected first Doppler images.

7. The method as claimed in claim 1, further comprising a rephasing procedure to compensate refractive aberrations of the eye, wherein said rephasing procedure comprises:
   the estimation of a corrective phase term from said first Doppler image; and,
   the calculation, for each hologram of said first plurality of holograms, of a compensated hologram, wherein said calculation uses said corrective phase term.

8. The method as claimed in claim 7, wherein said corrective phase term is expressed in terms of a linear combination of Zernike polynomials.

9. The method as claimed in claim 7, wherein said estimation of a corrective phase term from said first Doppler image comprises an iterative procedure.

10. The method as claimed in claim 7, wherein said estimation of a corrective phase term from said first Doppler image comprises a digital wavefront estimation of the phase term made from inter-correlation of the Doppler images calculated in sub-apertures.

11. A digital holography device for full-field blood flow imaging of ocular vessels of a field of view of at least a first layer of the eye, comprising:
- an optical source configured for the generation of an illuminating beam and a reference beam, wherein said illuminating beam is configured for illuminating said at least first layer;
- a combining element configured for combining the said reference beam and a part of said illuminating beam that is backscattered from the said at least first layer;
- a two-dimensional optoelectronic detector of frame rate, configured to acquire a plurality of interferograms wherein an interferogram is defined as the signal resulting from the interference between the said reference beam and a part of said illuminating beam that is backscattered from said at least first layer;
- a processing unit configured for processing said plurality of interferograms, wherein said processing comprises:
- the calculation, for each interferogram of said plurality of interferograms, of a hologram, wherein the hologram is defined by a complex amplitude of a light beam backscattered by said at least first layer in a given spatial plane, resulting in a first plurality of holograms;
- the selection, in sequential time windows, of second pluralities of holograms from said first plurality of holograms;
- the calculation, for each said second plurality of holograms, of a Doppler power spectrum;
- the calculation, based on said Doppler power spectrum, of at least a first Doppler image thus generating at least a first plurality of Doppler images associated with said plurality of sequential time windows;
- the processing of each first Doppler image, wherein said processing comprises:
  - the devignetting of said first Doppler image, resulting in a devignetted first Doppler image;
  - the normalization of said devignetted first Doppler image based on a spatial average of an intensity of said first Doppler image, resulting in a normalized first Doppler image;
  - the subtraction, from said normalized first Doppler image, of said spatial average of said intensity of said first Doppler image, resulting in a corrected first Doppler image; and,
- the sequential assembling of said corrected first Doppler images to generate a movie showing an evolution over time of blood flows in said ocular vessels.

12. The device as claimed in claim 11, further comprising an optical element configured for changing the size of said field of view.

13. The device as claimed in claim 11 wherein the optical source is a single-mode external cavity diode laser.

14. The device as claimed in claim 11, wherein the two-dimensional optoelectronic detector is a camera of CCD or CMOS type.

15. The device as claimed in claim 14, wherein the frame rate of said optoelectronic detector is inferior to about 10 kHz.

16. The device as claimed in any one of claim 11, wherein the frame rate of said optoelectronic detector is inferior to about 10 kHz.

* * * * *